United States Patent
Baigar et al.

(10) Patent No.: US 9,360,413 B2
(45) Date of Patent: Jun. 7, 2016

(54) POSITIONING MEANS FOR A MEASURING CELL

(71) Applicant: DIONEX SOFTRON GMBH, Germering (DE)

(72) Inventors: Erik Baigar, Munich (DE); Christian Andreas Hilmer, Germering (DE); Andreas Unger, Garching (DE)

(73) Assignee: DIONEX SOFTRON GMBH, Germering (DE)

( * ) Notice: Subject to any disclaimer, the term of this patent is extended or adjusted under 35 U.S.C. 154(b) by 0 days.

(21) Appl. No.: 14/200,404

(22) Filed: Mar. 7, 2014

(65) Prior Publication Data

US 2014/0268126 A1    Sep. 18, 2014

(30) Foreign Application Priority Data

Mar. 12, 2013    (DE) .......................... 10 2013 102 440

(51) Int. Cl.
*G01N 21/01* (2006.01)
*G01N 21/05* (2006.01)
*G01N 30/74* (2006.01)

(52) U.S. Cl.
CPC ................ *G01N 21/01* (2013.01); *G01N 21/05* (2013.01); *G01N 30/74* (2013.01)

(58) Field of Classification Search
CPC .................... G01N 21/00; G01N 21/05; B01J 2219/00281; B01J 19/0046
USPC .................. 356/244, 246, 440; 422/401, 554, 422/82.05; 435/287.7
See application file for complete search history.

(56) References Cited

U.S. PATENT DOCUMENTS

| | | | |
|---|---|---|---|
| 3,332,316 A | 7/1967 | Saunders |
| 3,552,864 A | 1/1971 | Shields |
| 4,076,420 A | 2/1978 | De Maeyer et al. |
| 4,178,067 A | 12/1979 | Johnson et al. |
| 4,575,424 A | 3/1986 | Allington et al. |
| 4,580,901 A | 4/1986 | Goldsmith |
| 4,588,893 A | 5/1986 | Vidrine et al. |
| 4,747,687 A | 5/1988 | Hoppe et al. |
| 4,886,356 A | 12/1989 | Paradis |
| 5,003,174 A | 3/1991 | Datwyler et al. |

(Continued)

FOREIGN PATENT DOCUMENTS

| | | |
|---|---|---|
| CN | 201000423 Y | 1/2008 |
| CN | 201464357 U | 5/2010 |

(Continued)

OTHER PUBLICATIONS

Barka et al., "Wege zur Miniaturisierung von Analysensystemen," Tiel 3: Automatische probeninjektion, LaborPraxis, Nov. 1997.

(Continued)

*Primary Examiner* — Hoa Pham
(74) *Attorney, Agent, or Firm* — Timothy J. Ohara

(57) ABSTRACT

The invention relates to a positioning means for a flow cell used for optical detection, comprising a base having at least one contact face, the contact face being provided to make contact with the end of the flow cell, wherein the base has at least one reference face, which is to be aligned and/or positioned relative to the flow channel of a flow cell, and wherein the base is designed to receive a connecting piece in such a way that the latter assumes a predefined attitude and alignment relative to the flow channel.

14 Claims, 4 Drawing Sheets

(56) References Cited

U.S. PATENT DOCUMENTS

| | | |
|---|---|---|
| 5,097,211 A | 3/1992 | Schonstedt |
| 5,139,333 A | 8/1992 | Reinhard |
| 5,140,169 A | 8/1992 | Evens et al. |
| 5,240,537 A | 8/1993 | Bodicky |
| 5,417,925 A | 5/1995 | Goodale et al. |
| 5,650,846 A | 7/1997 | Yin et al. |
| 5,814,742 A | 9/1998 | Vissers et al. |
| 5,905,271 A | 5/1999 | Wynn |
| 6,122,049 A | 9/2000 | Sugiyama et al. |
| 6,188,813 B1 | 2/2001 | Dourdeville et al. |
| 6,200,531 B1 | 3/2001 | Liljestrand et al. |
| 6,315,958 B1 * | 11/2001 | Singh-Gasson et al. ...... 422/554 |
| 6,444,175 B1 * | 9/2002 | Singh-Gasson et al. ...... 422/553 |
| 6,484,569 B1 | 11/2002 | Plant et al. |
| 6,526,188 B2 | 2/2003 | Dourdeville et al. |
| 6,587,195 B1 | 7/2003 | Jennings |
| 6,747,740 B1 | 6/2004 | Leveille et al. |
| 6,867,857 B2 | 3/2005 | Hobbs |
| 7,184,141 B2 | 2/2007 | Brewer et al. |
| 7,948,621 B2 | 5/2011 | Burns et al. |
| 2002/0038998 A1 | 4/2002 | Fujita et al. |
| 2003/0118485 A1 | 6/2003 | Singh-Gasson et al. |
| 2004/0027568 A1 | 2/2004 | Maiefski et al. |
| 2004/0036987 A1 | 2/2004 | Wisecarver et al. |
| 2004/0066509 A1 | 4/2004 | Canty et al. |
| 2004/0080744 A1 | 4/2004 | Hobbs |
| 2005/0104607 A1 | 5/2005 | Byington et al. |
| 2005/0213088 A1 | 9/2005 | Brewer et al. |
| 2007/0041009 A1 | 2/2007 | Iwano et al. |
| 2007/0064226 A1 | 3/2007 | Kolp et al. |
| 2007/0077546 A1 | 4/2007 | Ji et al. |
| 2008/0113447 A1 * | 5/2008 | Krager et al. ............... 436/172 |
| 2010/0118298 A1 * | 5/2010 | Bair ................... G01N 15/1404 356/246 |
| 2011/0180211 A1 | 7/2011 | Jurischka et al. |
| 2011/0299067 A1 | 12/2011 | Yokoyama et al. |
| 2014/0266266 A1 * | 9/2014 | Baigar et al. ................ 324/693 |

FOREIGN PATENT DOCUMENTS

| | | |
|---|---|---|
| CN | 201765178 U | 3/2011 |
| DE | 3603905 A1 | 8/1986 |
| DE | 3605518 A1 | 8/1987 |
| DE | 102007048738 | 4/2009 |
| DE | 102008027026 A1 | 12/2009 |
| JP | 4873193 | 10/1973 |
| JP | 59180448 | 10/1984 |
| JP | 60148956 | 10/1985 |
| JP | 02042337 | 2/1990 |
| JP | 02134563 | 5/1990 |
| JP | 05187995 | 7/1993 |
| JP | 8500188 | 1/1996 |
| JP | 9178648 | 7/1997 |
| JP | 2007047176 | 2/2007 |
| JP | 2011007758 | 1/2011 |
| WO | 2005015162 A2 | 2/2005 |
| WO | 2007009493 A1 | 1/2007 |
| WO | 2011079058 A1 | 6/2011 |
| WO | 2013113402 A1 | 8/2013 |

OTHER PUBLICATIONS

Dionex Corporation, PDA-100 (USB) Photodiode Array Detector Operator's Manual, Revision 03, Mar. 2006, 132 pages.

Dionex Corporation, UVD 170U and UVD 340U UV/VIS Detectors Operating Instructions, Revision 1.0-a, Jul. 2003, 54 pages.

Van Der Vlis, "Development of a needle device for on-line electroextraction-liquid chromatography," J. Chromatogr. A, 741, 13-21, 1996.

Vissers et al., "A fully automated microautosampler for micro and capillary liquid chromatography," International Laboratory, Jan. 1996.

* cited by examiner

POSITIONING MEANS FOR A MEASURING CELL

CROSS REFERENCE TO RELATED APPLICATIONS

This application is claims the priority benefit under 35 U.S.C. §119 to German Patent Application No. 10 2013 102 440.8, filed on Mar. 12, 2013, entitled "Positioning means for a measuring cell" the disclosure of which is incorporated herein by reference.

FIELD OF THE INVENTION

The present invention relates to a positioning means for a measuring cell for optical detection, such as is used in the area of HPLC (high performance liquid chromatography).

BACKGROUND

By means of such measuring cells, for example, the variation over time of the transmission of an eluting liquid is determined in order to obtain a chromatogram. The eluting liquid (below: sample) is led through the flow channel of a flow cell and irradiated with suitable light longitudinally or transversely with respect to the flow direction. The flow channel of the flow cell, through which the sample and the light are led, is usually formed as a thin tube with a diameter in the millimeter and sub-millimeter range.

DE 36 03 905 A1 discloses a through-flow particle analyzer, in which a suspension is examined by shining light in. An objective structure, spaced apart by a layer of dispersion oil, adjoins a flow cell, from which reflected light for evaluation enters the objective structure.

U.S. Pat. No. 7,184,141 B2 describes an optical flow cell, in which a liquid to be examined is conveyed and is transilluminated transversely with respect to the conveying direction, in order to be able to draw conclusions about the liquid by using the evaluation of the emerging light.

An optical measuring cell is further also disclosed by US 2011/0299067 A1.

SUMMARY

In one embodiment of the detection, the light is radiated into the tube along the axial direction thereof via an optical conductor. According to one variant, the optical conductor must be positioned as accurately centrally as possible with respect to the tube axis and, between itself and the inner wall of the tube, form an annular gap, through which the sample flows into the tube. The exactly central positioning of the optical conductor and the resultant formation of a uniform annular gap are particularly advantageous here to optimizing the flow. The central alignment is, however, not absolutely necessary, according to the general idea of the invention; the accurate arrangement of the optical conductor in a predefined relative position and attitude in relation to the tube is important.

The optical conductor is usually introduced into the tube by means of a specific connecting piece; the sample is also fed to the tube at the same time via the connecting piece. For the accurate arrangement of the optical conductor within the tube, it is therefore necessary to align the connecting piece exactly relative to the tube. Here, the optical conductor should assume an arrangement in space of which the attitude (position) and angle of rotation (alignment) are determined by the tube, for example collinearly and/or centrally with respect thereto.

The object of the invention was therefore to offer a device for ensuring the accurate arrangement of an optical conductor within the tube. The object was further the creation of a method for ensuring the exact positioning.

In order to hold the previously described tube stably, a flange in particular is suitable, which carries the tube in a central opening, the end face of the tube preferably ending flush with the surface of the flange facing away from the tube, following a machining step. At the other end of the tube, a further corresponding flange can be provided; both flanges can also hold a protective pipe, within which the tube is arranged and located protected. Such an arrangement (with or without protective pipe) is to be designated a flow cell below. The outer face of a flange, facing away from the tube, forms one end of the flow cell. At this end, in practice the connecting piece having the optical conductor and the sample feed are arranged and connected, attention having to be paid to the aforementioned exact arrangement (alignment and positioning) of the optical conductor and of the connecting piece relative to the tube held in the flange.

This accurate alignment is made possible by a positioning means according to the invention. The positioning means comprises a base which, in a preferred embodiment, is designed to be at least partially rotationally symmetrical. However, it can also have the form of a prism or another body, provided that there is at least one predefined guide surface which is parallel to the desired insertion direction of the optical conductor. The base has a contact face, which is provided to make contact with the end of the flow cell. The contact face is preferably designed to be flat, as is the end of the flow cell. The imaginary axis of rotation of a partially rotationally symmetrical base in the application extends collinearly with respect to the tube axis in the area of the tube opening; the insertion movement of the connecting piece can take place along this axis of rotation.

Furthermore, the base has a reference face, which is intended to be arranged relative to the opening of the tube arranged in the end of the flow cell. In particular, the reference face can be a rotationally symmetrical face of the base, for example a section of a cylindrical outer face. The reference face is used to arrange the positioning means relative to the tube opening, so that the positioning means assumes a defined attitude relative to the tube in terms of position and alignment in space. The alignment and/or positioning of the connecting piece relative to the positioning means can likewise be carried out by means of this reference face but can also be achieved by other faces on the base with which the connecting piece interacts as it is inserted.

Furthermore, the base comprises an insertion region for the insertion of the connecting piece to be centered relative to the flow cell and to the tube. According to the invention, as a result of being pushed into the insertion region, the connecting piece is aligned by means of contact with the base (preferably with the reference face of the latter) and fixed in its radial position such that, as it is pushed further in, the optical conductor carried by the connecting piece is inserted centrally into the opening of the tube in the end of the flow cell. The positioning means thus constitutes a constructively simple but effective aid to the accurate and simple alignment of the connecting piece on the flow cell, it being assumed that the positioning means already inherently has an accurately predefined attitude relative to the tube opening when the connecting piece is pushed in.

According to a particularly expedient embodiment of the invention, the base is designed to be annular or tubular. The comparatively simple geometric shape is sufficient to achieve the desired centering effect. In particular, as a result of contact with the outer or inner circumferential surface of the annular or tubular base, the connecting piece can be aligned and positioned radially as it is inserted into the base. The contact face on the flange of the flow cell of an annular or tubular base is then formed by the front end of the ring or tube and has the form of a circular annular face.

In a modified embodiment of the base, the latter is formed as a pot structure. The pot likewise comprises an annular or tubular section but which is closed at one end by a bottom. The outer side of the bottom forms the contact face to make contact with the end of the flow cell, the bottom having a preferably central bottom opening for the optical conductor to be fed through and for the sample to be fed in, so that a connecting piece with the optical conductor inserted into the pot can project through the central opening. Given prior exact alignment of the positioning means relative to the tube opening in the end of the flow cell, the optical conductor comes centrally into the opening of the tube. The pot structure, as compared with the annular or tubular form, has the advantage of a greater contact area and/or offers more space for channels and cut-outs on the flange or on and in the pot bottom to receive adhesive material adjacent to the end of the flow cell. Such profiling of the contact face facing the end permits the specific local application of adhesive, preferably in the profile ways, in order for example to keep adhesive away from the tube or a sealing surface surrounding the latter and to offer compensation space for excess adhesive.

According to a further advantageous embodiment of the invention, the base is additionally equipped with guide means, which are intended to facilitate the insertion of the connecting piece. These can be chamfered areas at the end of the base facing away from the flow cell, which pre-center the connecting piece as it is inserted. As it is pushed further in, the connecting piece is then aligned accurately, preferably in contact with the reference face, within the scope of the selected manufacturing tolerances. In addition to the pre-centering, the guide means can also serve to fix a specific angle of rotation of the connecting piece about the tube axis, at which angle the latter is to be inserted into the base. This appears to be expedient in particular when the connecting piece is not formed completely rotationally symmetrically, for example when the sample feed leads laterally into the connecting piece.

In order to arrange the connecting piece relative to the flow cell with the aid of the positioning means, it is necessary to connect the positioning means to the flow cell and, in particular with reference to the opening of the tube, to align and/or to position said positioning means accurately in the end of the flow cell, the insertion direction being intended to coincide with the alignment of the tube axis. An appropriate method comprises the following method steps:

a) arranging the positioning means on the end of a flow cell;
b) positioning the positioning means with at least one reference face thereof relative to an opening present in the end of the flow cell;
c) fixing the positioning means on the flow cell in order to maintain the relative position established under b).

During the positioning according to method step b), the positioning means is positioned relative to the tube opening and optionally additionally aligned with respect to the angle of rotation about the tube axis. This is done in relation to the reference face of the positioning means. The base is displaced and positioned and/or aligned such that the at least one reference face assumes a predefined position and/or orientation relative to the tube opening. If this reference face is, for example, the cylindrical inner circumferential surface of a tubular base, then the reference face (and, with it, the base) would have to be aligned concentrically with respect to the tube opening. Of course, in this case it is assumed that the connecting piece guides its optical conductor likewise centrally and later, as it is inserted into the base, is aligned centrally on the latter.

The subsequent fixing of the positioning means on the end of the flow cell according to step c) can be carried out in particular by adhesive bonding; this is to be understood in the further sense as the production of an adhesive connection between base and flow cell, for example by using an adhesive. Alternatively, mechanical fixing means (screws, clamping elements, etc.) are suitable for fixing, it being necessary to factor in more overall space and mechanical stresses that may possibly occur. It is necessary to avoid undesired forces which could be introduced into the connection during the fixing, which impairs the previously undertaken alignment of the base on the flow cell. However, for repeated use, for example, the positioning means can also be connected detachably to the flow cell, for example in the form of a preferably multi-part pot structure, which is clamped on the flange or held on the flange by a union nut.

Expediently, the alignment of the base on the end of the flow cell can be carried out by using optical aids, for example with a microscope. Particularly suitable is the use of imaging computer means, in which the position of the base relative to the tube opening can be displayed well on a monitor.

In step a), the flow cell having the tube opening could be moved, by using the optical aid (for example a camera, monitor or image-processing software), into an intended position, in which the center of the tube opening appears in the center of the monitor, for example. For this purpose, a camera could be directed at the end, approximately perpendicular thereto. In a following step, the base is then placed on the end and displaced in such a way that, in the image thereof on the monitor, its reference face accurately assumes the desired relative position and/or alignment with respect to the tube opening. In addition, the orientation of the rotary attitude of the base relative to the flow cell is set in this way, in order for example to move a cut-out in the wall of the base into the correct position. An adhesive previously or subsequently arranged between base and flow cell can then be cured, the reference face of the positioning means preferably being fixed centrally in relation to the tube opening. During the subsequent insertion of the connecting piece, the optical conductor held centrally by the latter then preferably comes centrally into the tube opening. The use of optical aids permits a magnified pictorial representation of the individual components, which is useful for the precise alignment, given the small dimensions of the tube opening and of the optical conductor. In addition, the aforementioned displacement can be carried out in an aid constructed specifically for this purpose, for example by using micrometer screws, or even automatically by using the data from the camera. This increases the accuracy and reproducibility of the method. In the above-described method, the end of the flow cell with the tube opening located flush therein is further removed from the camera than the base subsequently placed on the end of the flow cell, which, with the end thereof facing away from the flow cell, is then located closer to the camera or the lens of the latter. During the subsequent optical adjustment of the base relative to the tube opening, it is therefore possible for the problem to arise that the base with its reference face and the tube opening then located somewhat further away cannot be depicted sharply at the same time, which makes the optical adjustment more difficult. In order to overcome this problem, a special embodiment of the method provides that, before the arrangement of the flange of the flow cell under the camera, a plane-parallel lens or a similar optical aid is introduced into the optical path between flange and camera, in order to lengthen this path (for example a BK7 lens). Following the focusing of the camera onto the flange surface through the lens, the flange can be displaced such that the tube opening imaged by the camera reaches an intended position of the image, for example the center of the image.

For the subsequent arrangement of the base relative to the flow cell and tube opening, said base is placed on the end of the flange of the flow cell. Following removal of the lens from the optical path, the camera (without active re-focusing by the camera itself) focuses at another depth which, given suitable selection of the lens, coincides accurately with the attitude and height of the reference face. This could be, for example, the upper side of a bottom of the base, which faces the camera and which, for example, is 1 mm thick and is therefore located 1 mm closer to the camera than the end of the flow cell flange. The base and therefore the image of its now sharply imaged reference face can likewise be displaced into the center of the image, which means that the desired arrangement of the base relative to the flow cell is carried out particularly simply and without re-setting the camera.

In order to increase the accuracy of the relative positioning, the steps of arranging the flange (with use of the lens) and of the base (without use of the lens) can be repeated, in order respectively to eliminate final deviations from the center of the image.

Following the formation of the adhesive connection between base and flow cell, the positioning means can reliably and accurately align the connecting piece that is to be inserted subsequently as it is inserted.

BRIEF DESCRIPTION OF THE DRAWINGS

The invention is to be explained in more detail below by using exemplary Figures.

DETAILED DESCRIPTION OF EMBODIMENTS

Figure 1:
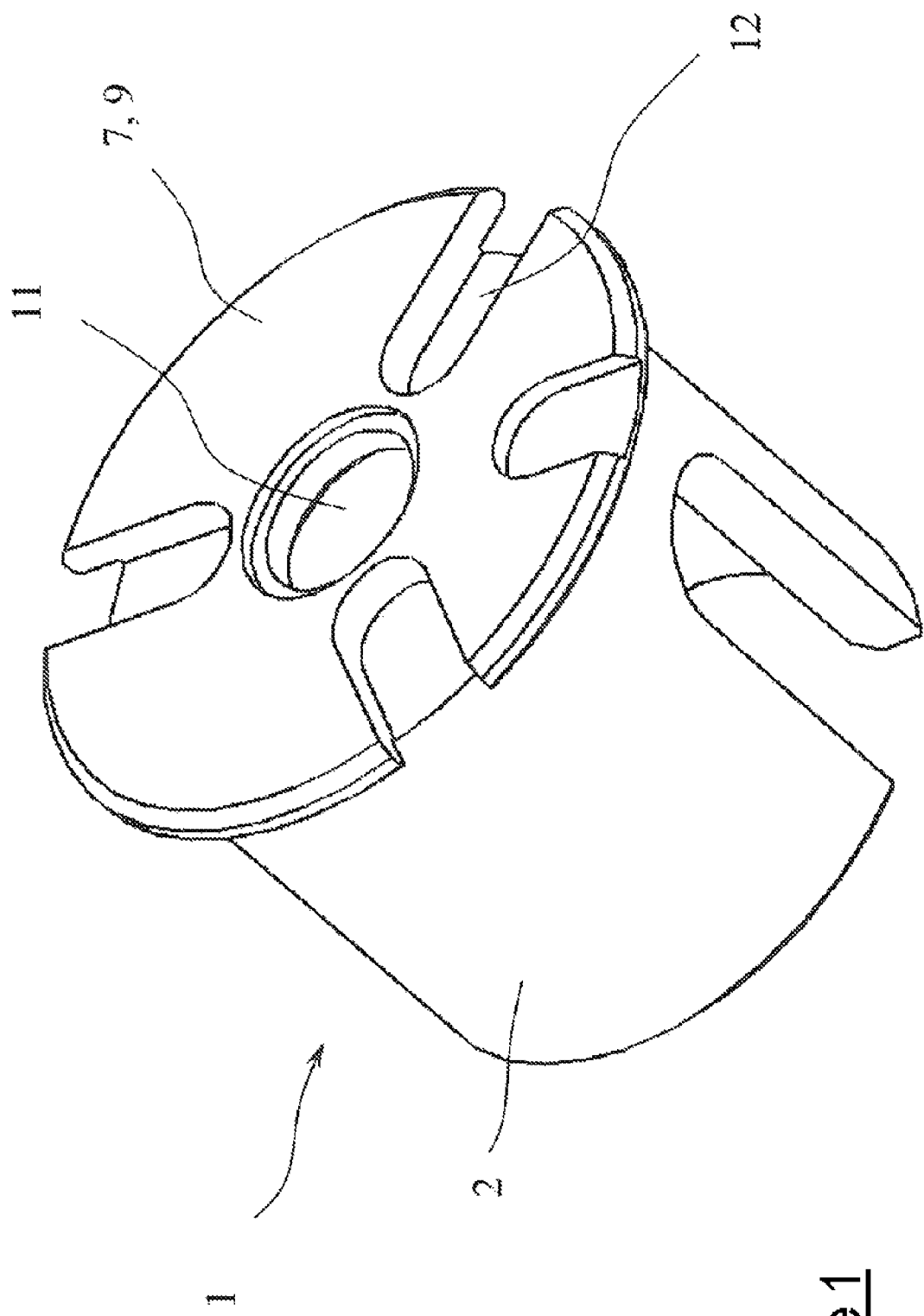
FIG. 1 shows a perspective simplified view of a first embodiment of a positioning means.

A substantially rotationally symmetrical positioning means 1 is illustrated in FIG. 1. It is formed by a base 2, which has a cylindrical structure and is closed at one end by a bottom 9. The bottom 9 simultaneously forms the contact face 7 to make contact with a flow cell 10 illustrated in FIG. 2. Approximately in the center of the bottom 9 there is arranged a bottom opening 11, through which an optical conductor and a fluid feed are to be guided later toward the flow cell. Optical conductor and fluid feed are held by a connecting piece, not shown, which can be inserted at the open end of the base 2 opposite to the bottom 9. On its contact face 7 formed by the underside of the bottom 9, the base 2 has a plurality of grooves 12, which are provided to receive an adhesive with which a connection between the base 2 and a flange of the flow cell 10 is to be produced.

Figure 2:
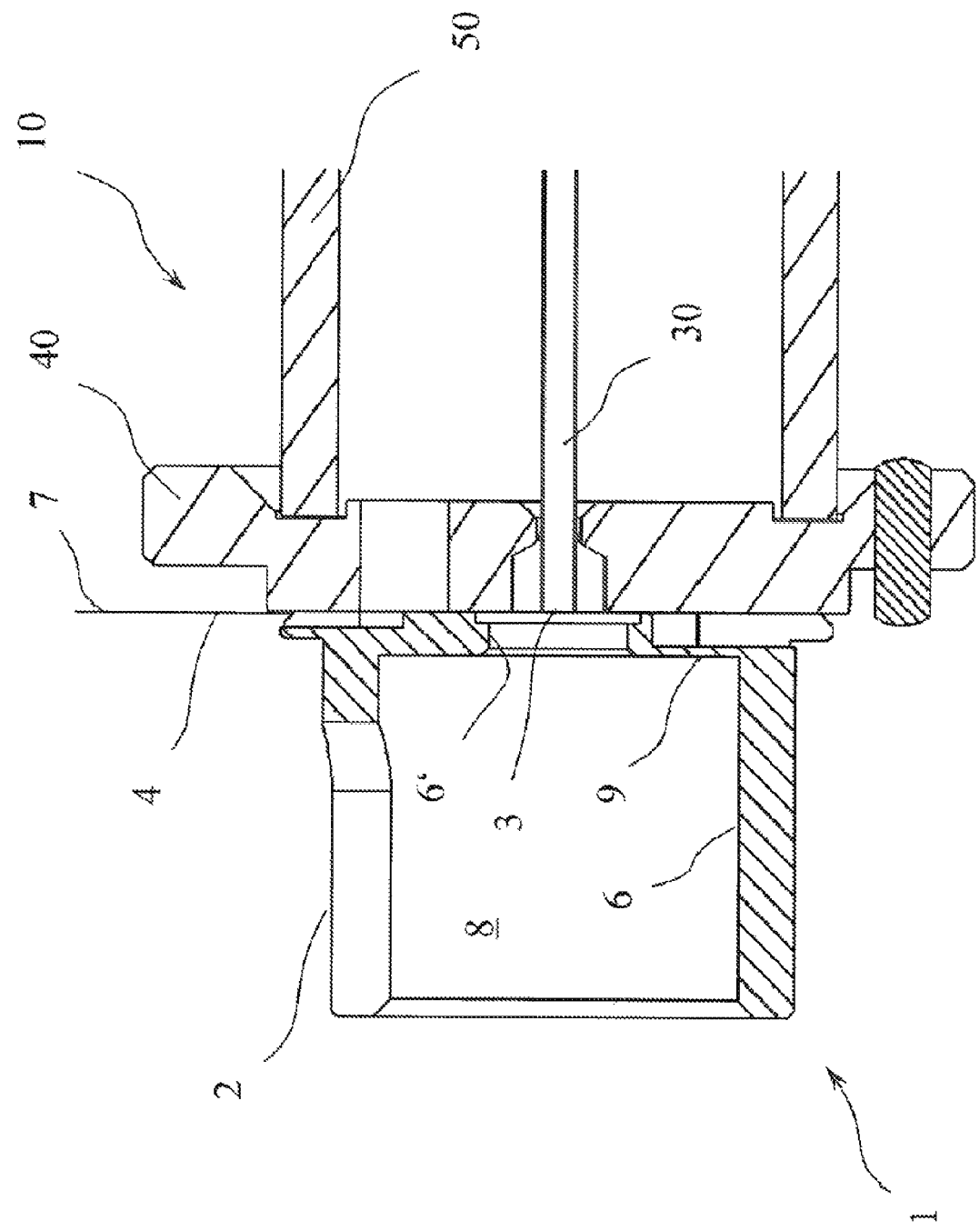
FIG. 2 shows the positioning means according to FIG. 1 in conjunction with a flow cell.

In FIG. 2 the positioning means 1 according to FIG. 1 can be seen in a section illustration and in horizontal orientation. Provided in the interior of the base 2 is an insertion region 8 to receive the connecting piece, not illustrated, which could be pushed into the insertion region from the left in FIG. 2. The inner wall of the base 2 serves simultaneously as reference face 6. The reference face 6 can be used to align the base 2 relative to the adjacent flow cell 10 and/or perform a guiding function for the connecting piece to be inserted, in order to align and to position the latter relative to the base.

The contact face 7 of the base 2 adjoins the end of a flow cell 10, shown only partly in FIG. 2. The flow cell 10 comprises a flange 40, which in the center carries a tube 30, through which a fluid is to be led. In order to protect the tube 30, the latter is surrounded by a protective pipe 50, which is likewise fixed to the flange 40. In order to be able to insert the optical conductor exactly into the tube 30, the positioning means 1 according to the invention is provided, which is to be arranged on the end 4 of the flange 40 in order, as the connecting piece carrying the optical conductor is inserted, to insert said optical conductor accurately into the tube 30 and to fix the attitude and position thereof relative to the tube 30. The positioning means illustrated in FIG. 1 is placed on the flange 40 for this purpose and is aligned relative to the opening 3 of the tube 30 which ends flush with the end 4 of the flange 40. In the exemplary embodiment, the reference face 6' running around the opening 11 in the bottom 9 is aligned concentrically with respect to the opening 3 of the tube 30 for this purpose. A connecting piece pushed into the insertion region 8 of the base 2 and which guides the optical conductor centrally therefore pushes the latter into the tube 30 in accurate alignment via face 6 and positioned via face 6' as it is inserted.

Via the grooves 12, illustrated in FIG. 1, on the contact face 7 facing the end 4 of the flange 40, an adhesive can be introduced before or after the positioning of the base on the flange 40, in order to produce a permanent connection between positioning means 1 and flange 40. The grooves 12 according to FIG. 1 do not reach as far in the radial direction as the central bottom opening 11, so that adhesive cannot reach this central region either and therefore come into contact with the optical conductor.

Figure 3:
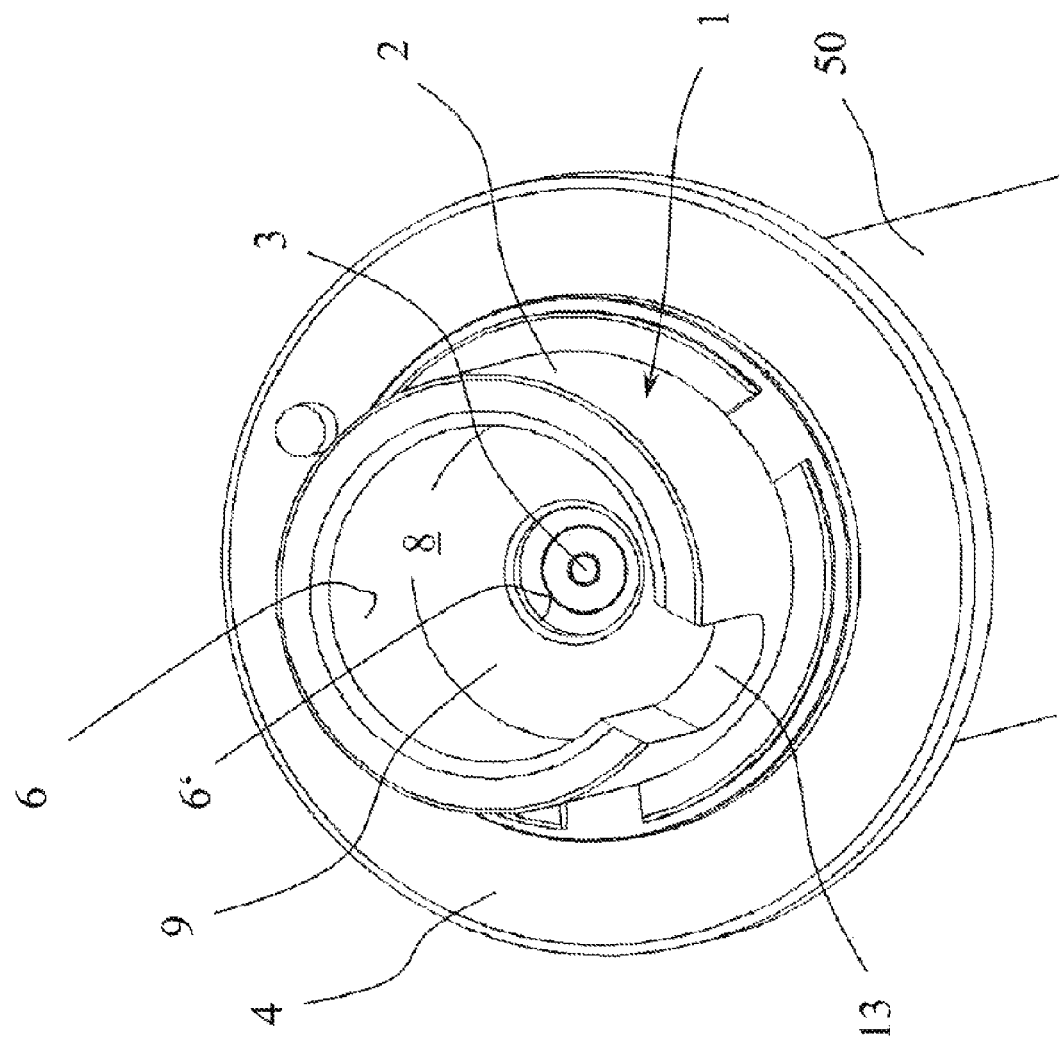
FIG. 3 shows the arrangement according to FIG. 2 in a perspective view.

FIG. 3 shows the arrangement according to FIG. 2 in a perspective illustration. Here, the base 2 exhibits a feed cut-out 13 in its cylindrically shaped wall. Through this feed cut-out 13, a connecting part projecting laterally out of the connecting piece, not illustrated, can be guided, for example in order to permit the feeding of the sample medium into the connecting piece and to fix the rotational attitude around the tube axis.

Figure 4:
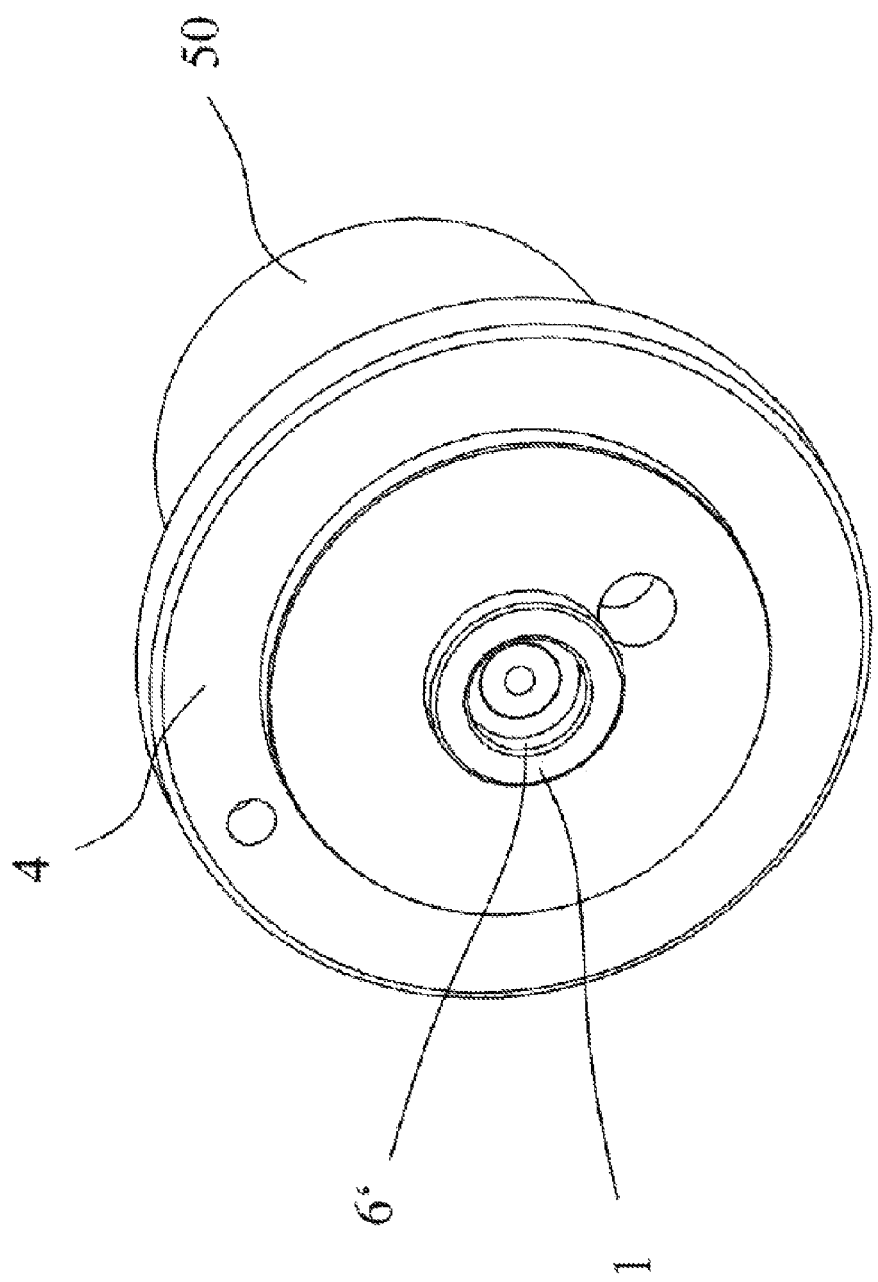
FIG. 4 shows a simplified form of a positioning means according to the invention.

FIG. 4 shows a highly simplified embodiment of the positioning means 1 on the end 4 of a flow cell. This positioning means 1 is implemented as a simple ring without bottom. Depending on the requirements on the accuracy during the positioning and alignment of the positioning means on the flow cell and of the connecting piece on the positioning means, very simply shaped reference faces and contact faces, such as the inner wall 6' of the ring, following the pattern of FIG. 4, may be adequate.

LIST OF DESIGNATIONS

1 Positioning means
2 Base
3 Opening
4 End
6, 6' Reference face
7 Contact face

8 Insertion region
9 Bottom
10 Flow cell
11 Bottom opening
12 Groove
13 Feed cut-out
30 Tube
40 Flange
50 Protective pipe

What is claimed is:

1. A positioning device to position a flow cell used for optical detection, the positioning device comprising:
   a) a base having at least one contact face, the contact face configured to make contact with an end face of the flow cell,
   b) wherein the base has at least one reference face, which is configured to be aligned relative to a flow channel of the flow cell,
   c) wherein the base is configured to receive a connecting piece, the connecting piece having a predefined attitude and alignment relative to the flow channel, and
   d) wherein the end face is formed by an outer face of a flange of the flow cell, facing away from the flow cell, and the end face provides for the arrangement or connection of the connecting piece to an optical conductor and a sample feed.

2. The positioning device according to claim 1, in that the base is annular or tubular, and the contact face is formed by an end of the base that faces the flow cell.

3. The positioning device according to claim 1, in that the base is a pot structure having at least one opening in a bottom, an outer side of the bottom forming the contact face.

4. The positioning device according to claim 1, in that the base has a guide to initially align a connecting piece to be inserted into an insertion region during an insertion movement, whereby, as the connecting piece is pushed further in, effect an exact positioning of the connecting piece relative to the base.

5. A method to position a flow cell using a positioning device to position a flow cell used for optical detection, the positioning device comprising: base having at least one contact face, the contact face configured to make contact with an end face of the flow cell; wherein the base has at least one reference face, which is configured to be aligned relative to a flow channel of the flow cell; wherein the base is configured to receive a connecting piece, the connecting piece having a predefined attitude and alignment relative to the flow channel, and wherein the end face is formed by an outer face of a flange of the flow cell, facing away from the flow cell, and the end face provides for the arrangement or connection of the connecting piece to an optical conductor and a sample feed, the method comprising:
   a) arranging the positioning device on the end face of the flow cell, the end face being formed by an outer surface of a flange of the flow cell, facing away from the flow cell, and being provided for the arrangement or connection of a connecting piece to an optical conductor and a sample feed;
   b) positioning and orienting the positioning device with at least one reference face thereof relative to an opening present in the end face of the flow cell;
   c) fixing the positioning device on the flow cell to maintain a relative position established under step b).

6. The method according to claim 5, in that the positioning in accordance with step b) is carried out by using optical aids in conjunction with an imaging computer.

7. The method according to claim 5, further comprising:
   i) arranging a plane-parallel lens between a camera and the end face to lengthen the optical path, with focusing of the camera onto the end face;
   ii) displacing the flow cell with the end face such that an image of the end face supplied by the camera is in an intended position,
   iii) removing the lens and displacing the positioning device according to step b) such that an image of the reference face supplied by the camera is in an intended position.

8. The method according to claim 5, in that, during the positioning, the opening is aligned centrally with respect to a circular reference face.

9. A flow cell comprising a positioning device to position a flow cell used for optical detection, the positioning device comprising:
   a) a base having at least one contact face, the contact face configured to make contact with an end face of the flow cell,
   b) wherein the base has at least one reference face, which is configured to be aligned relative to a flow channel of the flow cell,
   c) wherein the base is configured to receive a connection piece, the connecting piece having a predefined attitude and alignment relative to the flow channel, and
   d) wherein the end is formed by an outer face of a flange of the flow cell, facing away from the flow cell, and the end face provides for the arrangement or connection of the connecting piece to an optical conductor and sample feed.

10. The flow cell according to claim 9, in which the flange centrally holds a tube in an opening located in the end face.

11. The flow cell according to claim 10 further comprises at least one connecting piece positioned and aligned in the base via the positioning device.

12. The flow cell according to claim 10, in which the optical conductor is positioned centrally with respect to a tube axis of the tube, in which an annular gap forms between the optical conductor and an inner wall of the tube.

13. The flow cell according to claim 9, in which the connecting piece holds the optical conductor.

14. The flow cell according to claim 9, in which the sample feed leads laterally into the connecting piece.

* * * * *